United States Patent [19]

Pieronne et al.

[11] Patent Number: 4,662,355

[45] Date of Patent: May 5, 1987

[54] PUMP REGULATION DEVICE

[76] Inventors: Alain Pieronne, 18 Rue Francois de Badts, 59110 La Madeleine; Georges Soots, 17 Rue Bazinghien, 59000 Lille; Régis Logier, 19 Rue des Liliums, 59134 Herlies; Michel Delecroix, 2 rue d'Haubourdin, 59155 Faches Thumesnil, all of France

[21] Appl. No.: 723,955

[22] PCT Filed: Aug. 6, 1984

[86] PCT No.: PCT/FR84/00185
  § 371 Date: Apr. 4, 1985
  § 102(e) Date: Apr. 4, 1985

[87] PCT Pub. No.: WO85/00754
  PCT Pub. Date: Feb. 28, 1985

[30] Foreign Application Priority Data
  Aug. 8, 1983 [FR] France ................ 83 13236

[51] Int. Cl.4 .................................... A61M 1/03
[52] U.S. Cl. ......................... 128/1 D; 623/3
[58] Field of Search ........... 128/1 D, DIG. 3; 604/4, 604/5, 6, 67, 66, 50, 118; 623/3

[56] References Cited

U.S. PATENT DOCUMENTS

| | | | |
|---|---|---|---|
| 3,457,909 | 7/1969 | Laird | 128/1 D |
| 3,771,174 | 11/1973 | Wortman | 128/DIG. 3 |
| 4,080,958 | 3/1978 | Bregman | 128/1 D |
| 4,116,589 | 9/1978 | Rishton | 128/1 D X |
| 4,223,672 | 9/1980 | Terman et al. | 604/5 |
| 4,334,180 | 6/1982 | Bramm et al. | 128/1 D X |
| 4,459,977 | 7/1984 | Pizon et al. | 128/1 D |
| 4,486,189 | 12/1984 | Troutner et al. | 604/5 |
| 4,493,693 | 1/1985 | Bilsted et al. | 604/6 |
| 4,540,399 | 9/1985 | Litzie et al. | 128/1 D X |

FOREIGN PATENT DOCUMENTS

2455229 5/1976 Fed. Rep. of Germany ..... 128/1 D

Primary Examiner—John J. Vrablik
Assistant Examiner—Theodore Olds
Attorney, Agent, or Firm—Kerkam, Stowell, Kondracki & Clarke

[57] ABSTRACT

The invention provides a pump regulation device. It is characterized in that the device (21) comprises: means for recording the real pressure (24) and a reference pressure, means, on the one hand for comparing the real pressure (24) in the organ and the reference pressure and, on the other hand, for emitting a signal proportional to the error, ports controlling the threshold of this error signal, an alarm controlled by the signal passing through at least one of said ports.

9 Claims, 8 Drawing Figures

PUMP REGULATION DEVICE

The invention relates to a device and to a process for regulating a pump.

It applies more particularly but not exclusively, in the medical field, to the regulation of the by-pass circuit of a "left vent" system or of an artificial kidney or more especially of a left side assistance system possibly coupled to a right side assistance system, whether the flow in the circuit is continuous or pulsed.

Although left ventricle by-passes were recognized very soon as being full of promise in the treatment of serious cardiogenic shock, present techniques are in general insufficient for treating cardiogenic shocks following a massive myocardium incompetence met with in "post extra-corporal circulation" commonly called "post-C.E.C".

Only a left side assistance system, possibly associated with a right side assistance system may ensure the perfusion of the peripheral tissues providing balance favorable to possible recovery of the myocardium.

The beneficial effects of this new balance between the assistance and the energy demand have been demonstrated on animals.

It is in fact the complete discharge of the left ventricle, for which the assistance device is substituted, which provides an improvement in the perfusion characteristics of the myocardium. The balance thus obtained provides then:

high level coronary perfusion, a reduction of the volume of the ventricle and of the sub endocardial pressure and, a reduction in the consumption of oxygen because no external work is accomplished by the heart.

The left side assistance is then meant for sick persons who, because of the state of the myocardium, cannot be weaned from the "C.E.C" despite the use of catecholamines and of the intra-aortic counter-pulse.

Left side assistance for several days allows the myocardium then to recover. Such assistance for several days has also allowed 50% of sick people of this type to be weaned.

The flow in the circuit may be continuous but in the present state of knowlede, it seems important to provide a pulsed flow for several reasons such as attenuation of the response to stress of extra corporal circulation (C.E.C) by reducing the release of catecholamines with as a result:

reduction of the systemic vascular resistances and so a reduction of the cardiac work, reduction of the suprarenal hypophyseal hormone releases.

Such a left side assistance circuit obviously requires the left auricle pressure, called hereafter "POG" to be monitored for sudden flow, pressure and volemie variations would not be borne very well by patients under cardiogenic shock.

Moreover, if the pressure becomes negative, by a suction effect which occurs, a risk of collapse of the pulmonary veins would appear and so a risk of air embolism.

The advantage of automatic regulation is all the greater since these circuits are generally put in place for several days.

During all this time the circuit must be monitored so as to avert all dangers such as hyper pressure, line breakage, clogging of the filter, air embolism.

It is then inconceivable to use them without having the security, in particular, of automatic regulation and alarms.

For ensuring an even blood flow but also for avoiding the accidents mentioned above, one result which the invention aims to obtain is a device which regulates the blood flow in the organism and so which, in the example chosen, regulates the left ventricle by-passes and which if need be, may also drive a simultaneous right ventricle by-pass circuit.

For this, it provides a regulating device for a pump which is particularly characterized in that it comprises:

means for recording the real pressure of the organ called hereafter "P.O.G"

means for recording a reference pressure, means on the one hand for comparing the P.O.G. with the reference pressure and, on the other hand, for emitting a signal proportional to the error, ports for controlling the threshold of this error signal, alarms controlled by the signal passing through at least one of said ports.

The invention also relates to a process for regulating this pump.

The invention will be better understood from the following description, given by way of non limitative example, of a left assistance circuit, with reference to the accompanying drawings which show schematically.

Figure 1:
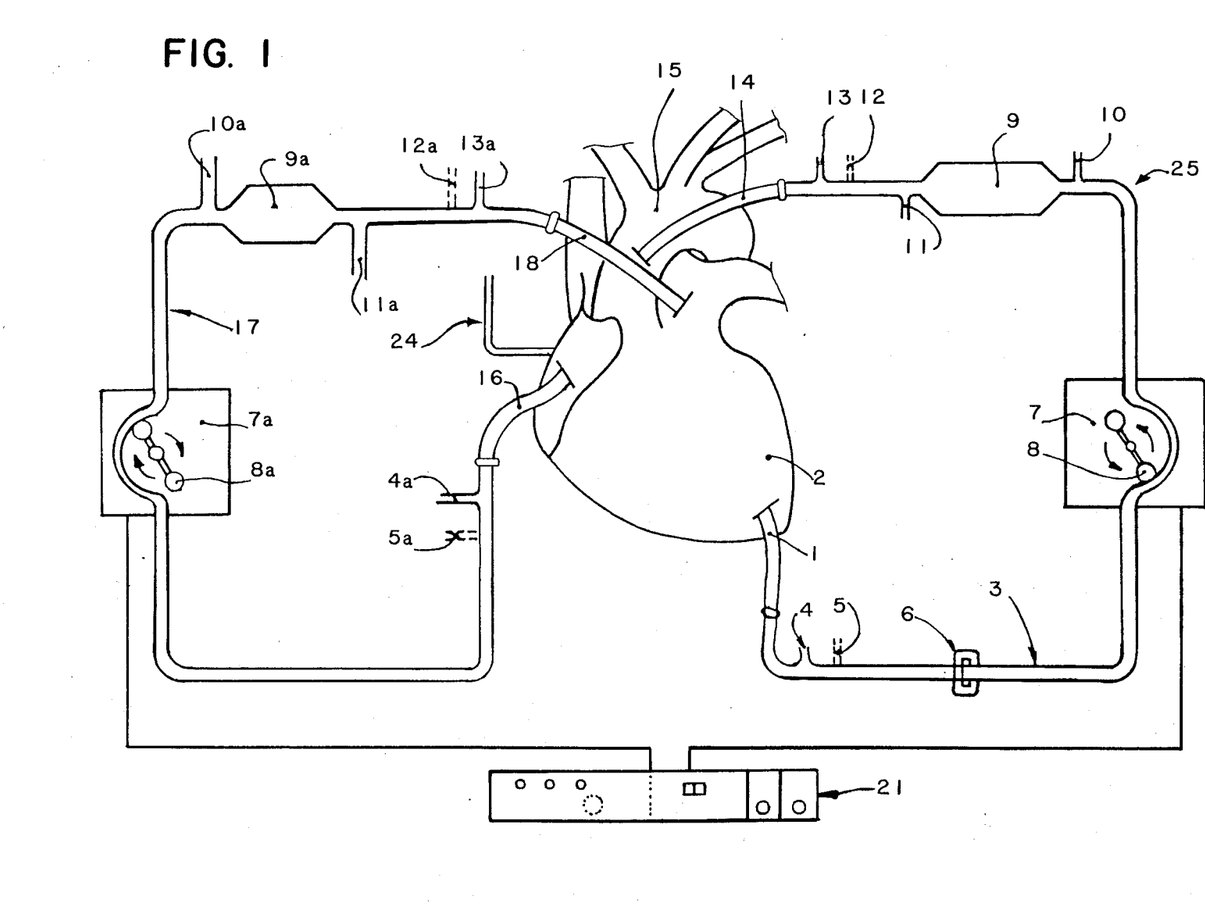
FIG. 1: an assistance circuit.

Referring to the drawings, it can be seen that the circuit such as the one for a left assistance C.E.C comprises a cannula 1 stitched to the organ such as the tip of the left ventricle 2 or the left auricle and which ensures the discharge of this organ.

It is connected by a non metallic connection (not shown), made for example from polyvinyl chloride, to the input of a circuit 3.

This circuit, called "arterial line", passes first of all through an air purge 4 then through a possible input 5 for a product such as heparine and a bubble detector 6 before arriving at a pump 7 with rotary rollers 8 whose speed is adjustable depending on the potential difference applied to its terminals.

It will for example be a pump of a design currently used for extra-corporal circulation.

On leaving pump 7, the arterial line passes through an upstream filter 9, downstream of which are provided two outlets 10, 11 which allows pressure measurements to be taken on each side of filter 9 which is itself interchangeable.

Before arriving at a second cannula 14 intended for reinjection into the inlet of the organ, for example at the level of the aorta 15, the circuit 3 continues by passing possibly through a system without heparine and through an input 12 for a product such as protamine, then through a new air purge 13.

As for the possible right assistance C.E.C. it is similar to the proceding one since it comprises for example, a first of all a cannula 16 stitched to the outlet of the organ, such as the vena cava and which, through a non metal connection, is connected to a circuit 17 passing first of all through an air purge 4b and a possible input 5a for a product such as heparine before reaching a pump 7a then an upstream filter 9a, downstream of which outlets 10a, 11a, allow pressure measurements to be made.

On leaving filter 9a, and after passing through a possible input 12a for a product such as protamine and a second air purge 13a, the circuit is connected to a pulmonary cannula 18.

Means are connected to the bubble detector 6 of the left system circuit for stopping the pump 7 should bubbles be detected.

Because of the upstream position of pump 7, despite the reaction time of said pump, the risk of injection of bubbles into the circuit is overcome.

As mentioned above, the pump 7, 7a is of a type whose flow rate is related to the potential difference applied to its terminals. For adjusting this potential difference as a function of the information taken from this circuit, the circuit comprises a regulating device 21.

This device operates particularly by reference to the real pressure in the organ, which pressure is hereafter called "P.O.G", and to a desired pressure called reference or preprogrammed pressure.

Thus, first of all, it comprises means for recording a reference pressure and means 24 for measuring the real pressure.

Figure 2:
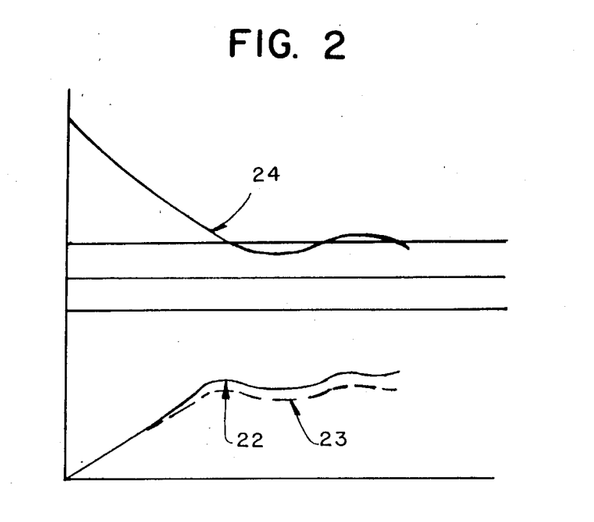
FIG. 2: the curves of the flow rate and of the P.O.G. during start up of the assistance C.E.C.

In two or three minutes, during start up of the assistance not only the flow rate in the left circuit 3 but also that flow rate in the possible right side circuit 17 increase according to a predetermined slope so as to arrive at an optimum flow rate.

During this time, the real pressure in the organ (P.O.G) decreases symmetrically with the flow rate.

As soon as the preprogrammed pressure is reached, the device of the invention comes into play which, for this, comprises means comparing the P.O.G. and the preprogrammed pressure which passes through ports so that:

if the P.O.G drops below the given value, the device reduces the flow rate so as to tend to increase the P.O.G as long as this latter remains less than the reference and, if the P.O.G rises above the value, the device increases the flow rate again so as to lower the P.O.G in the same proportions, until the flow rate is obtained which corresponds to the preprogrammed pressure.

The alarm ports are such that, if the real P.O.G signal drops by a value less than a given value (for example 5 mm of mercury), they cause a sound alarm and pump stoppage.

To resume operation, this pump will then have to be reset manually and we have the same case as mentioned above for starting up the assistance circuit.

In the case of left side cardiac assistance, with the right side of the heart operating, with the pump stopped and with the flow rate therefore zero, the P.O.G should rise.

It is only if, with left side assistance alone, the optimum cardiac index is not reached and if there exists a low left side auricle pressure with high venous pressure or an oxygen arterial pressure less than or equal to 60 mm of mercury, that complementary right side assistance should be envisaged.

The regulating device 21 further comprises means for comparing the pressure measured at the output 11 downstream of filter 9 with respect to a given preprogrammed pressure value, different from the reference pressure, and means for comparing the pressures at the outputs 10,11 upstream and downstream of said filter, the difference of these pressures causing the filter clogging alarm.

In combination with a bend 25 in the part of the circuit situated downstream of pump 7, the first means detect any hyperpressure.

Should a fixed threshold be overshot, this controls a sound alarm and a visual alarm indicating the type of problem which caused the pump to stop.

When this difference reaches a given preprogrammed value, said means then actuate the sound and visual alarms indicating this type of problem. In a variant, said device also comprises a means for the semi-quantitative evaluation of bubbles with auditive checking.

The device further comprises a weaning system by decrementing the assistance flow for example by about 100 ml every hour.

Figure 3:
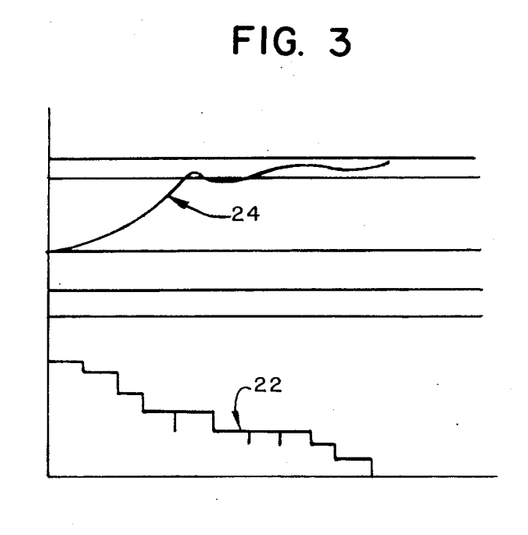
FIG. 3: the curves of the flow rate and of the P.O.G during weaning.

For weaning, so as to take into account the myocardium condition, the reference pressure will then be preprogrammed to a fairly high level then, the flow rate will be decremented as long as with the lower flow rate thus obtained, the preprogrammed pressure is not exceeded and this decrementation may continue until weaning is complete, if the preprogrammed pressure is exceeded, the above mentioned means will cause, on the one hand, the immediate stopping of the decrementation and return to the immediately prior flow rate as well as the setting off of a visual and sound alarm and, on the other hand, at the end of a certain time for example the following hour, a new attempt at decrementation.

The device may also comprise a "reset" key for stopping the sound alarm, the visual alarm remaining lit as long as the fault lasts. If this fault occurs several times, two solutions may then be envisaged:

either continuing the assistance by manually stopping the weaning attempt, or choosing another reference pressure level allowing decrementation to be resumed.

The maintenance of the assistance flow at a desired level may obviously be achieved by varying the level of the P.O.G by other means and, for example:

by adjusting the post-charge by means of vaso-dilators (soda nitroprussiate), by adjusting the pre-charge by "filling" the sick person (transfusion).

These sick people, whose bleeding is considerable at the beginning of this type of assistance, have of course a regulation of the central venous pressure (second pressure). This pressure is not entered into the present device for ensuring the regulation, but its value is nevertheless taken into account for determining the alarms.

In the case mentioned above, where the addition of a right side assistance is necessary, the flow rate of the corresponding pump 7a will be regulated by the samd device 21 as that of the left side assistance pump 7.

For this, since the flow rates are physiologically identical, within one or two percent (less 10% for coupled assistance) the device will simply comprise a means, such as a potentiometer, for varying, in sufficient proportions, the right side flow with respect to the left side flow, by adjusting the potential difference applied to the terminals of the right side pump 7a with respect to that of the left side pump 7, for example from +10% to −15%.

At the beginning of C.E.C these means will ensure a zero difference then the adjustment will be made depending on the adaptation of one heart with respect to another.

In a variant, the means for varying this potential difference and so the flow rate are driven by the P.O.G.

This adjustment is of course pointless if the remaining contractility is sufficient to provide regulation alone.

As mentioned above, the regulation of the pump flow is achieved by means of a DC voltage which is caused to vary, for example, from zero to 15 volts.

In the case where a pulsed flow is desired, the device is provided with means for overmodulating this voltage.

With the patient of course, in all cases, under the constant supervision of an electrocardiograph, the device may comprise means such that the electrocardiogram obtained may be advantageously entered into the regulator which then comprises, on the one hand, means for shaping the electrical inter-systolic space called "R.R space" and on the other hand, two potentiometers (FIG. 8) for determining, with respect to the preceding R.R. space, the duration, the time and the intensity of acceleration of the pump, independently of any other factor.

The pulse beginning will take place between 0 and 60% of the R.R. time, the pulse end being 40 and 100% of the R.R. time.

Depending on the pump pattern used, the amplitude is adjusted so as to allow diastolic ejection of 20 to 40 ml.

Figure 4:
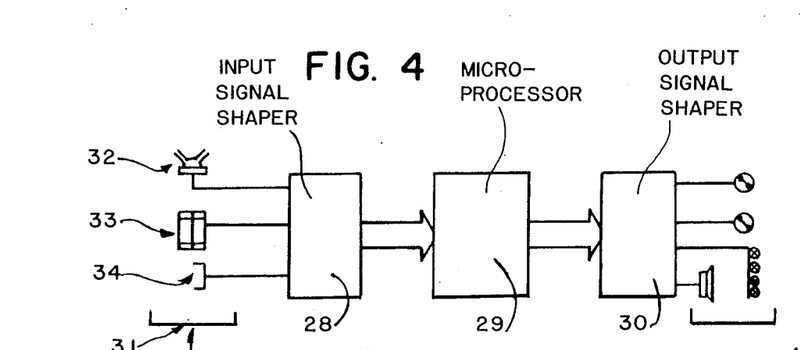
FIG. 4: the block diagram of a device.

For reasons of facility in use and turning, the regulating apparatus 21 was constructed around a microprocessor of type called "Z80".

It is formed from three main blocks 28, 29, 30, namely:
 a block 28 for shaping the input signals,
 a computing block 29,
 a block 30 for shaping the output signals.

The input members 31 (FIGS. 4 and 5) of the block 28 for shaping the input signals comprise mainly a means 32 for inputting the P.O.G taken by means 24, coding wheels 33 and inputs 34 coming from safety means.

Figure 5:
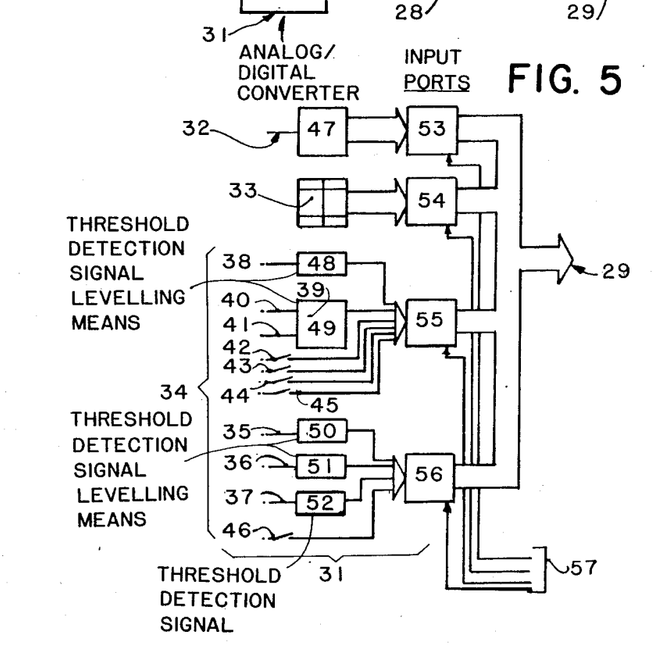
FIG. 5: the detail of the inputs of the device.

For using the P.O.G, block 28 should comprise a means 32 for transforming the P.O.G into an electric voltage and this means 32 should be such that it gives not only the voltage representing the instantaneous pressure but also the voltages corresponding to the high and low alarms of the P.O.G.

The coding wheels 33 will give to the computer 29 the P.O.G value to be reached (reference pressure) so that it may consequently match the flow rate thereto.

The inputs 34 from the safety means will be of two main types comprising, those controlling stopping of the pump and those controlling so called "normal" alarms.

Three inputs control the stopping of the pump:
 the input 35 corresponding to the signal of the P.O.G less than a fixed limit,
 the input 36 of the signal from the post-filter pressure sensor which, in combination with the bent circuit, detects a high pressure in the C.E.C circuit
 the input 37 for the signal from the bubble detector 6 fitted to the C.E.C circuit.

The inputs controlling normal alarms comprise the input 38 of a signal from the pressure module and indicating a P.O.G greater than a fixed limit and the input of the signal 39 representing the pressure difference calculated from the pressures 40 and 41 coming from the pre and post filter inputs 10, 11 of the circuit and signalling if the filter 9 is clogged.

The different input members 31 further comprise means such as:
 a resetting knob 42 for resetting the C.E.C should stoppage occur following an alarm,
 a weaning-regution inverter 43: for choosing between the regulation or weaning function,
 a knob 44 for stopping the sound alarms,
 a knob 45 for switching off the alarm indicator lights,
 a knob 46 for manually stopping the pump: it allows the user to stop the pump when he desires, and
 two linear potentiometers 26, 27 for on the one hand, varying the pump acceleration time with respect to the space R.R from 0 to 60% and, on the other hand, for varying the time when this pump acceleration is stopped with respect to space R.R from 40 to 100%.

When it is a pulsed flow the input to the device further comprises means (not shown) such as a:
 an "on/off" knob for the pulse system,
 a potentiometer for adjusting the pulsed volume,
 a knob for adjusting the amplitude of the pulses for example by means of a flip flop such as a trigger.

The circuit 28 for shaping the input signals (FIG. 4) comprises:
 means 47 transforming into logic signals the analog signals formed by the input magnitudes so that they may be processed by the computer 29 and
 means 48 to 51 for levelling the threshold detection signals 52.

Once these signals have been processed, they enter the computer 29 through input ports 53 to 56, for which the microprocessor has the controls 57 for this purpose.

As mentioned above, in the case of an assistance both for the left side and the right side, the regulation of the two circuits is provided nevertheless with respect to the same P.O.G.

The different alarm signals coming from the right circuit will even so be taken into account and, for this, the device will comprise the corresponding inputs which will, preferably, be fed to different ports, namely to a port 55 for the inputs controlling "normal" alarms and to a port 56 for the input controlling stopping of the pump 7, $7_a$.

Since the processing of these different signals from the right circuit is the same as for the signals from the left circuit, they have not been shown in the block diagram.

As already specified, the computer 29 (FIG. 7) is based on a type "Z80" microprocessor. With this microprocessor are associated:
 a read only memory 58 for the programmes,
 a random access memory 59 for the data,
 ordinary logic circuits 60 for decoding the memory addresses and the peripheral addresses, and
 a clock 61 driven by quartz.

Figure 7:
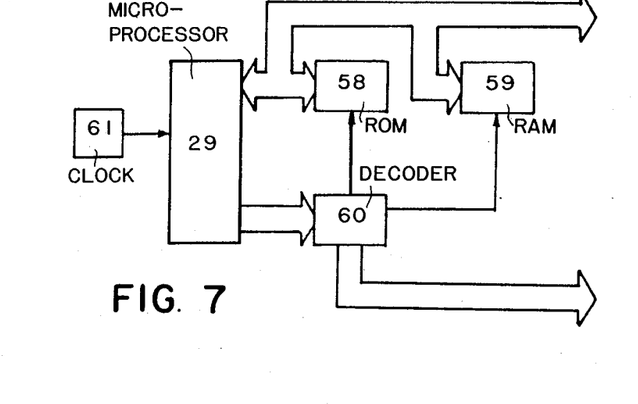
FIG. 7: the detail of the computer of the device.

After processing the input information, the computer 29 delivers, among other signals, a command which is intended for the pump but which is of digital type and which must be transformed into an electric voltage beforehand.

In fact, pump 7, $7_a$ uses, for its regulation, a DC or modulated voltage between 0 and 15 volts.

This is the role of circuit 30 for shaping the output signals (FIGS. 4 and 6) whch therefore comprises digital-analog conversion means 62 and levelling means 63. The output circuit 30 further comprises means 64 to 70 for displaying the alarms such as light emitting diodes and a sound alarm 71 such as a loud speaker 72 energized by a low frequency oscillator 73.

Figure 6:
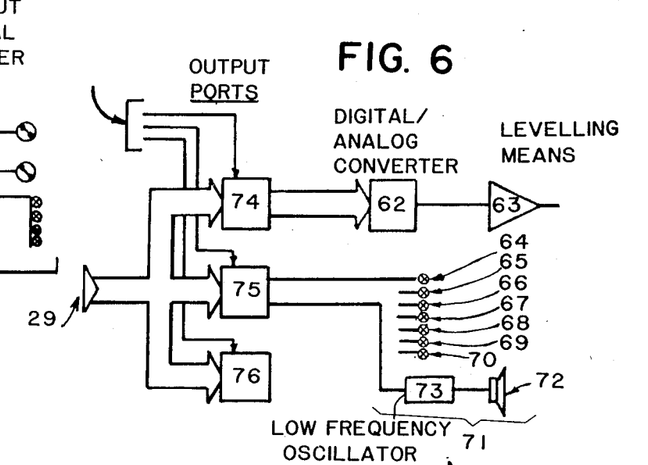
FIG. 6: the detail of the outputs of the device.

As for the input information, all this output information is delivered by the computer 29 via the output ports 74, 75, 76, the controls 77 of which are possessed by the microprocessor 29 for this purpose.

In the case of both left and right assistance, the device comprises a variable gain operational amplifier controlling the pump $7_a$ of the right side circuit from the signal for the left side pump 7.

Thus, the speed of the right side pump with respect to the left side pump will be adjustable manually by adjusting this gain. In the case of an anomaly either of the left side circuit or of the right side circuit, port 74 commands stopping of the two pumps whereas the alarms of the left side and/or right side circuit (not shown) are controlled through ports 75, 76 and the calculator 29.

Figure 8:
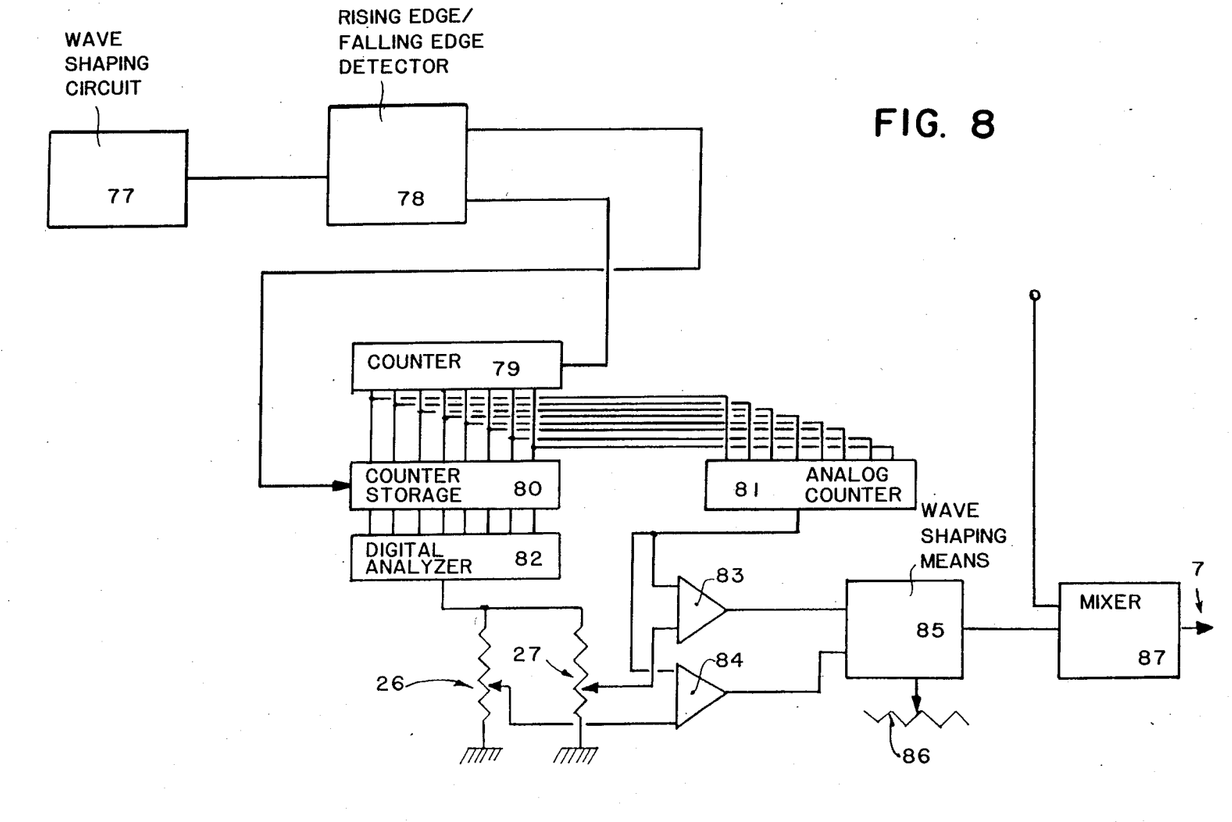
FIG. 8: a variant of the pump control for the case of a pulsed flow rate.

In the case of a pulsed flow, the assembly comprises:
a circuit 77 for shaping the wave,
a circuit 78 for detecting not only the falling edge, for resetting the counter 79 but also the rising edge, ensuring storage for counter 80,
an analog counter 81 for measuring the time R.R which is inverted and transformed into a potential difference by a digital analyzer 82,
two linear potentiometers 26, 27, for modulating the acceleration or deceleration time of pump 7,
a second digital analyzer controlled by the same counter 81,
two operational amplifiers 83, 84 which receive these modulated currents as well as the signals from the second digital analyzer.

Thus, are obtained, with respect to the space R.R, the acceleration rise time and the return to normal time. The signals then pass through a shaping means 85 then through a potentiometer 86 for levelling the pulsed volume before arriving at their mixer 87 with a signal coming from the microprocessor and called pump voltage.

Of course, another means for controlling the pulses, such as a flip flop or "trigger", may drive the circuit instead of the wave with a frequency varying from 60 to 120 hertz.

The regulation process takes place therefore in three phases:
from chosen pressure, called reference pressure, the apparatus progressively increases the pump output until the reference pressure is obtained at the level of the the auricle and the microprocessor then calculates the pump flow ratio with respect to the left auricle pressure and uses this constant for regulation purposes,
the flow of the pump is made proportional to the product of the left auricle pressure read multiplied by the calculated constant and the flow rate of the assistance pump then follows directly the value of the left auricle pressure read by the sensor for immediately compensating the deficit of the pump function of the heart and, if during regulation the value of the reference pressure is changed, for calculating a slope, the device behaving as a baroreceiver,
if there is recovery of the ad integrum of the heart, weaning takes place automatically by a decrementation of 100 ml/hour of the pump flow rate which continues by steps until a new given left auricle pressure value is obtained, even it is not reached until the pump is stopped, whereas, when this pressure is reached, a sound alarm is triggered off and the flow rate falls again to the previous value and the decrementation test is only begun again for the following hour with possibly a new left auricle pressure.

In the pulsed system, after reading and detection of the electrocardiogram QRS, in the diastolic phase, the flow is pulsed by accelerating the pump through, if the heart is undergoing ventricular fibrillation, an internal trigger with fixed frequency by possibly adjusting the rising edge and the falling edge with respect to the electrocardiogram as well as the amplitude of the pulse and of the duration.

We claim:

1. A regulation device (21) for regulating at least one pump included in a flow circuit within a circulatory flow system for bypass assistance of an organ, said system comprising cannulae (1) and (14) situated respectively at the level of an outlet (2) and of an inlet (15) of the organ to be assisted, said cannulae (1.14) being connected by non-metallic connections to a flow circuit, said flow circuit comprising:
a pump (7) with rollers (8) whose output is adjustable by adjusting the potential difference applied to its terminals,
a filter (9) with means (10, 11) for taking the pressure upstream and downstream of this filter (9),
means (24) for taking a real pressure in the organ,
at least one means for pulsing the output from the pump (7) and
air purging means (4, 13) disposed at the input and at the output of the circuit and an equal number of means (5, 12) for injecting products into said circuit, said regulation device comprising:
means for recording the real pressure in the organ and a preprogrammed reference pressure,
means for comparing said real pressure in the organ and the reference pressure and for emitting a signal proportional to the error,
output ports connected to receive said signal, and
alarm means controlled by the signal passing through at least one of said ports.

2. The device according to claim 3 wherein said flow circuit further comprises a bubble detector (6) placed upstream of the pump (7).

3. The device according to claim 1, wherein downstream of the pump (7), the circuit forms a bend (25) said device further comprising, combined with alarm means, means for controlling the pressure measured in the output (11) downstream of the filter (9) with respect to the reference pressure.

4. The device according to claim 1, further comprising, combined with alarm means, means for comparing the pressure (10, 11) upstream and downstream of said filter (9).

5. The device according to claim 1, further comprising a means for detection and semi quantitative evaluation of bubbles with auditive checking.

6. The device according to claim 1, further comprising a weaning system said weaning system operating by decrementing the assistance flow rate; and means for returning to a previous flow rate.

7. The device according to claim 1, which, in combination with a first assistance system comprises a second assistance system which, like the first one, comprises cannulae (16, 18) between which is connected, by means of non metallic connections, a flow circuit (17) comprising a pump ($7_a$), a filter ($9_a$), upstream and downstream of which outlets ($10_a$, $11_a$) allow pressure readings, said second assistance system being controlled by the same device (21) as, said first assistance system this device comprising at least one potentiometer bringing the potential difference applied to the terminals of the pump of the first assistance system to the value required by the pump of the second assistance system.

8. The device according to claim 7, further comprising means for varying the potential difference as a function of the real pressure in the organ.

9. The device according to claim 1, characterized in that at least one of the means comprises at least one microprocessor.

* * * * *

UNITED STATES PATENT AND TRADEMARK OFFICE
CERTIFICATE OF CORRECTION

PATENT NO. : 4,662,355
DATED : May 5, 1987
INVENTOR(S) : Pieronne et al

It is certified that error appears in the above-identified patent and that said Letters Patent is hereby corrected as shown below:

Column 8, line 40, "claim 3" should be --claim 1--.

Signed and Sealed this

Twentieth Day of October, 1987

*Attest:*

DONALD J. QUIGG

*Attesting Officer*  *Commissioner of Patents and Trademarks*